United States Patent
Walker et al.

(10) Patent No.: US 6,641,603 B2
(45) Date of Patent: Nov. 4, 2003

(54) HEAT EXCHANGE CATHETER HAVING HELICALLY WOUND REINFORCEMENT

(75) Inventors: Blair D. Walker, Mission Viejo, CA (US); Nora T. Pham, Lake Forest, CA (US)

(73) Assignee: Alsius Corporation, Irvine, CA (US)

(*) Notice: Subject to any disclaimer, the term of this patent is extended or adjusted under 35 U.S.C. 154(b) by 0 days.

(21) Appl. No.: 10/120,590

(22) Filed: Apr. 11, 2002

(65) Prior Publication Data

US 2002/0151944 A1 Oct. 17, 2002

Related U.S. Application Data

(60) Provisional application No. 60/283,332, filed on Apr. 13, 2001.

(51) Int. Cl.[7] .................................................. A61F 7/00
(52) U.S. Cl. ........................................ 607/105; 607/106
(58) Field of Search .......................... 607/96, 104–106, 607/113; 604/93.01, 93.05, 96.01, 97.01

(56) References Cited

U.S. PATENT DOCUMENTS

| | | | |
|---|---|---|---|
| 3,425,419 A | 2/1969 | Dato | |
| 4,038,519 A | 7/1977 | Fourcras | |
| 4,762,130 A | * 8/1988 | Fogarty et al. | 606/159 |
| 4,941,475 A | 7/1990 | Williams et al. | |
| 4,945,912 A | 8/1990 | Langberg | |
| 5,151,100 A | 9/1992 | Abele et al. | |
| 5,279,598 A | 1/1994 | Sheaff | |
| 5,370,616 A | 12/1994 | Keith et al. | |
| 5,383,856 A | 1/1995 | Bersin | |
| 5,484,411 A | * 1/1996 | Inderbitzen et al. | 604/103.08 |
| 5,486,208 A | 1/1996 | Ginsburg | |
| 5,498,261 A | 3/1996 | Strul | |
| 5,542,928 A | 8/1996 | Evans et al. | |
| 5,549,552 A | 8/1996 | Peters et al. | |
| 5,797,948 A | 8/1998 | Dunham | |
| 5,807,395 A | 9/1998 | Mulier et al. | |
| 5,899,899 A | 5/1999 | Arless et al. | |
| 5,919,187 A | 7/1999 | Guglielmi et al. | |
| 5,957,963 A | 9/1999 | Dobak, III | |
| 6,011,995 A | 1/2000 | Guglielmi et al. | |
| 6,051,019 A | 4/2000 | Dobak, III | |
| 6,096,068 A | 8/2000 | Dobak, III et al. | |
| 6,126,684 A | 10/2000 | Gobin et al. | |
| 6,149,677 A | 11/2000 | Dobak, III | |
| 6,190,356 B1 | 2/2001 | Bersin | |
| 6,224,624 B1 | 5/2001 | Lasheras et al. | |
| 6,231,594 B1 | 5/2001 | Dae | |
| 6,241,722 B1 | 6/2001 | Dobak et al. | |
| 6,245,040 B1 | * 6/2001 | Inderbitzen et al. | 604/103.07 |
| 6,251,129 B1 | 6/2001 | Dobak, III et al. | |
| 6,251,130 B1 | 6/2001 | Dobak, III et al. | |
| 6,254,626 B1 | 7/2001 | Dobak, III et al. | |
| 6,261,312 B1 | 7/2001 | Dobak, III et al. | |
| 6,264,679 B1 | 7/2001 | Keller et al. | |
| 6,287,326 B1 | 9/2001 | Pecor | |
| 6,312,452 B1 | 11/2001 | Dobak, III et al. | |
| 6,338,727 B1 | 1/2002 | Noda et al. | |

* cited by examiner

*Primary Examiner*—Roy D. Gibson
(74) *Attorney, Agent, or Firm*—John L. Rogitz

(57) ABSTRACT

A intravascular heat exchange catheter includes a catheter body having a proximal end connectable with a heat exchange fluid source and a distal end insertable into the vasculature of a patient to facilitate heat transfer with flowing blood. The core has at least one heat exchange fluid lumen for circulating heat exchange fluid within the catheter body. A heat exchanger, e.g. a balloon surrounds a portion of the proximal end of the catheter. The heat exchanger is in fluid communication with the heat exchange fluid lumen for enabling heat exchange fluid from the heat exchange fluid source to circulate through the core and the balloon. A wire, or similar retainer, wraps around the balloon to seal the balloon against the core, forming at least two heat exchange lumens between the balloon and the core.

20 Claims, 3 Drawing Sheets

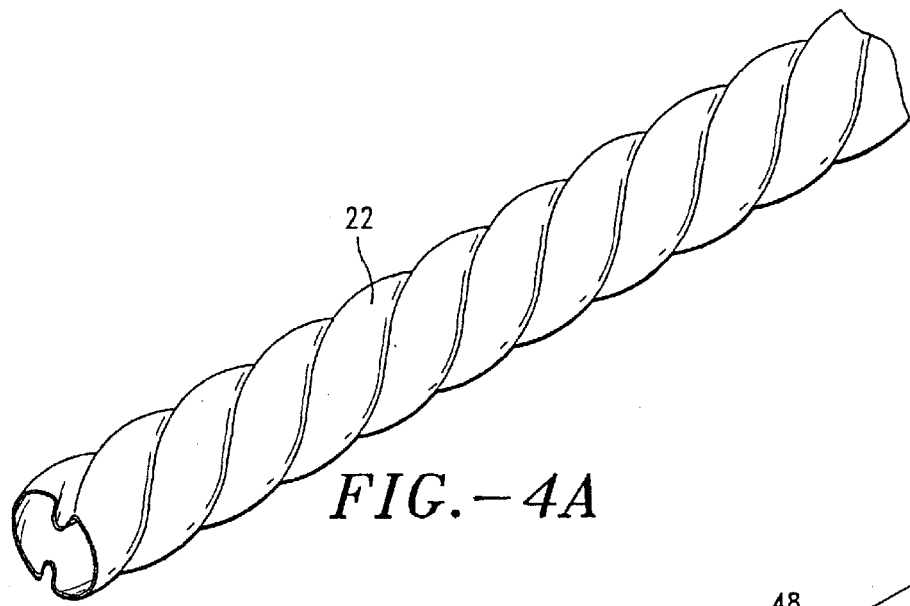
FIG.—4A
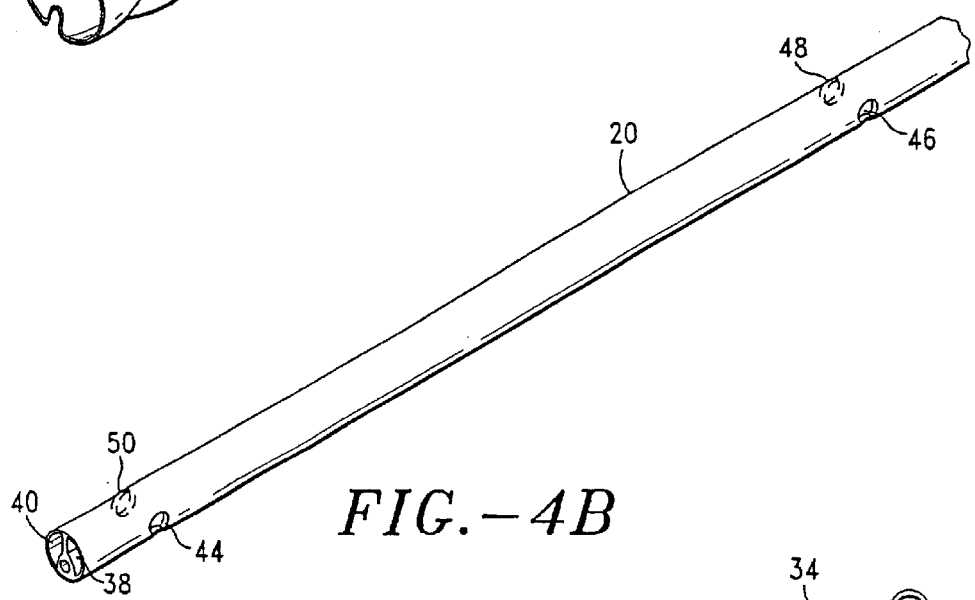
FIG.—4B
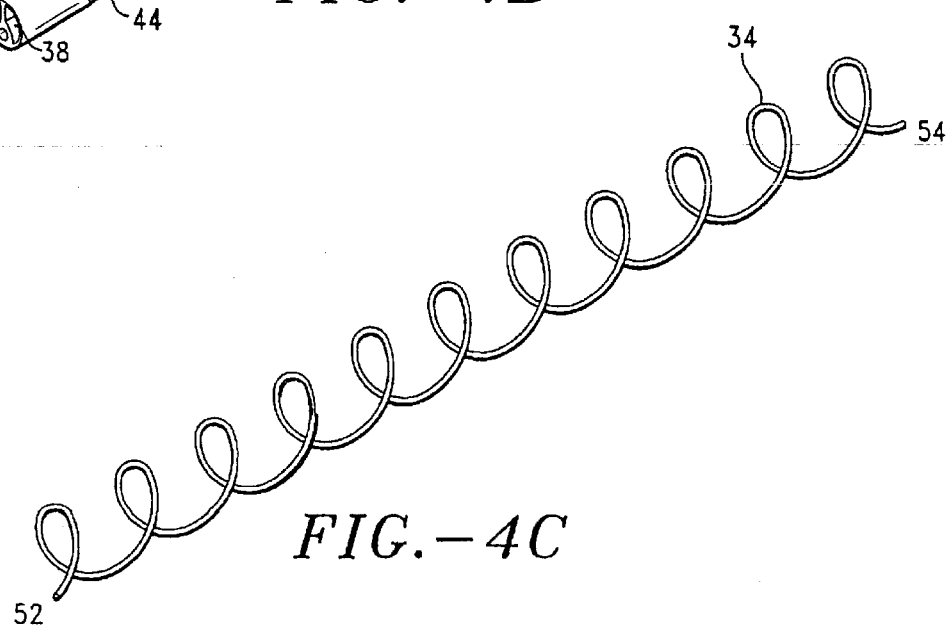
FIG.—4C

HEAT EXCHANGE CATHETER HAVING HELICALLY WOUND REINFORCEMENT

This application claims the benefit of Provisional Application No. 60/283,332, filed Apr. 13, 2001.

FIELD

This relates to intravascular heat exchange catheters, and more particularly to heat exchange catheters capable of circulating a heat exchange fluid.

BACKGROUND

Heat exchange catheters are used in many instances for a variety of reasons. Some surgeries, for example, are better performed when the patient cools to a hypothermic state. In other instances, a patient may suffer from accidental hypothermia and may need to be warmed to a normothermic temperature e.g. 98.6° F. Many heat exchange catheters include the capability of infusing fluids such as nutrition, medicine and contrast agents into the blood.

Post surgical patients risk infection and fever. A fever can be controlled through the use of a heat exchange system having an intravascular heat exchange catheter. One such system is disclosed in commonly assigned U.S. Pat. No. 6,146,411. This U.S. Patent is incorporated herein by reference and teaches an exemplary system used to achieve patient normothermia.

The principals of heat exchange applicable to any flowing medium (including blood) dictates the amount of heat transfer. In blood, the heat transferred depends on many things including the volumetric flow rate of the blood, the geometry of the heat exchanger and the temperature difference between the heat exchanger and the blood.

Blood has a maximum desirable heating limit. Beyond about 41° C., blood coagulates. This limits the maximum operating temperature of known intravasculature catheters. Because the operating temperature of an intravascular catheter is limited, the catheter geometry takes on an increased importance to effectuate overall heat transfer.

Commonly assigned U.S. Pat. No. 6,126,684, incorporated herein by reference, teaches a heat exchange catheter having smooth tubular balloons in serial alignment to exchange heat with the blood stream of a patient. The balloons each have an exterior surface that facilitates heat exchange with flowing blood.

U.S. Pat. No. 6,096,068 teaches a heat exchange catheter having a contoured outer surface and a heat exchange core. The contoured outer surface increases heat exchange surface area as compared to smooth tubular balloons. The contoured outer surface increases heat exchange fluid turbulence and flowing blood turbulence to improve heat transfer. These effects improve the heat transfer capability of the catheter.

What is desired is a heat exchange catheter with improves geometry to optimize heat transfer between the catheter and flowing blood. What is also desired is a heat exchange catheter that is easily manufactured, and which achieves optimal flexibility.

SUMMARY

A intravascular heat exchange catheter includes a catheter body having a proximal end connectable with a heat exchange fluid source and a distal end insertable into the vasculature of a patient to facilitate heat transfer with flowing blood.

The core has at least one heat exchange fluid lumen for circulating heat exchange fluid within the catheter body. A heat exchanger, e.g. a balloon surrounds a portion of the proximal end of the catheter. The heat exchanger is in fluid communication with the heat exchange fluid lumen for enabling heat exchange fluid from the heat exchange fluid source to circulate through the core and the balloon.

A wire, or similar retainer, wraps around the balloon to seal the balloon against the core, forming at least two heat exchange lumens between the balloon and the core. The wire has a helical configuration to seal the balloon against the core along a helical path.

Adhesive, according to one aspect of the invention bonds the balloon to the core along this helical path. According to a variation of the invention, the wire and the adhesive cooperate to maintain the balloon in a helical shape.

Maintaining the balloon in a helical shape can also be accomplished by heat treating the balloon to assume a particular nominal shape having a nominal surface contour. Ideally, the surface contour resembles a helix to enable the wire and/or adhesive to securely mate the balloon to the core without significant elastic resistance caused by balloon deformation.

The core defines a guidewire lumen, which connects with an infusion source for delivering medicine to the vasculature of the patient via the guidewire lumen.

BRIEF DESCRIPTION OF THE DRAWINGS

FIG. 4A shows a catheter balloon having a generally helically contour.

FIG. 4B shows a catheter core.

FIG. 4C shows a coil for sealing the balloon onto the catheter core.

DETAILED DESCRIPTION

Figure 1:
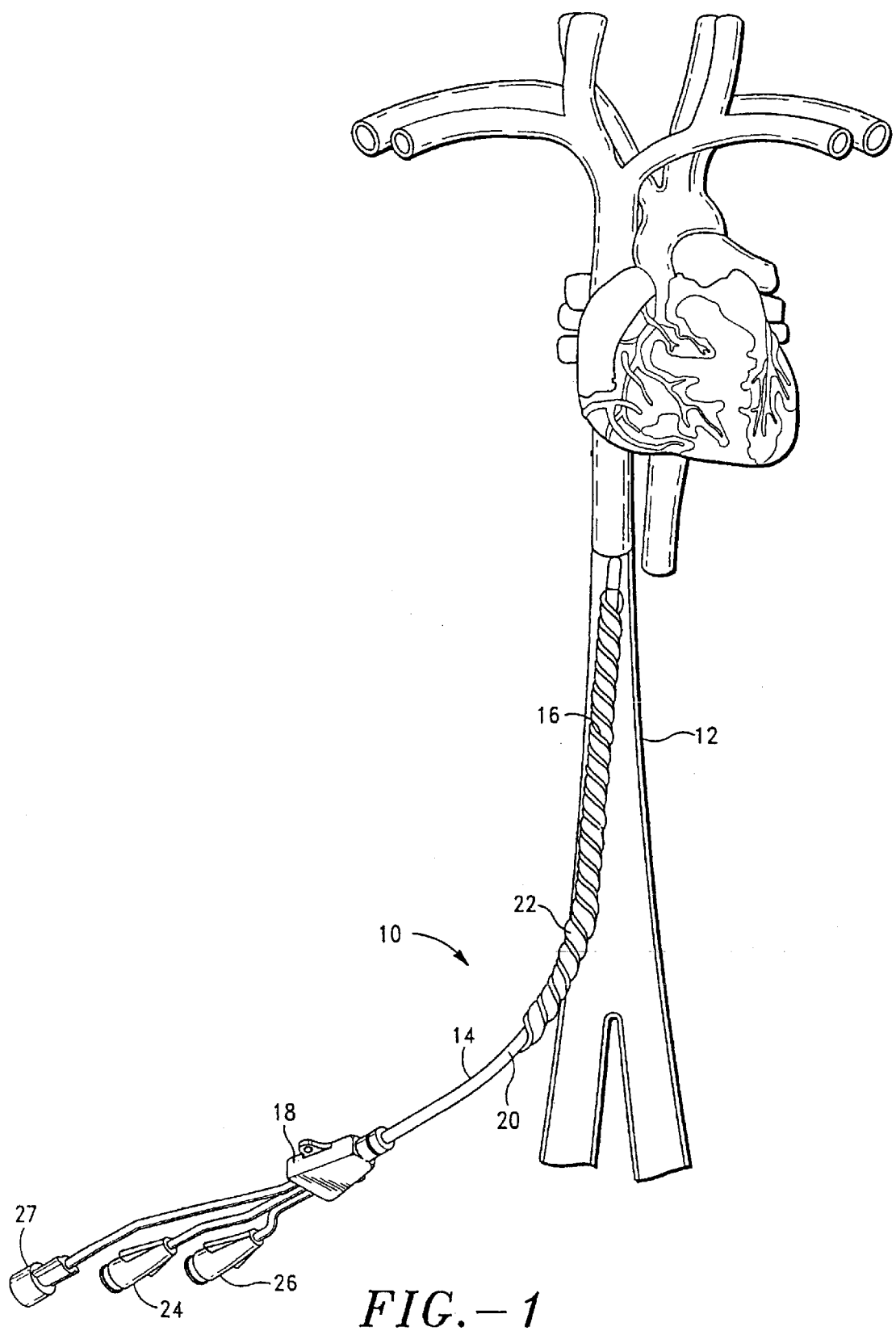
FIG. 1 shows a catheter inserting into the central vasculature of a patient.

FIG. 1 shows an intravascular heat exchange catheter generally designated with the reference numeral 10. The catheter 10 inserts into the central vasculature 12 of a patient.

The catheter 10 includes a catheter body 14 having a distal end 16 and a proximal end 18. The proximal end 18 is connectable with a heat exchange fluid source. The distal end 16 insertable into the central vasculature 12 to facilitate heat transfer with flowing blood. The distal end 16 is configured to facilitate blood flow through the central vasculature 12 so that the blood flow transfers heat between the catheter 10 and the patient.

The distal end 16 includes a core 20 with a spirally wrapped balloon 22. The balloon 22 is normally deflated and after insertion into the vasculature 12, the balloon 22 inflates with heat exchange fluid to assume a helical shape.

The proximal end 18 includes an inlet 24 and an outlet 26 for circulating heat exchange fluid through the catheter 10. Preferably, the core 20 defines a heat exchange fluid inlet lumen and a heat exchange fluid outlet lumen for circulating heat exchange fluid within the catheter body 14. The inlet 24 and outlet 26 communicate with the balloon 22 via the core heat exchange lumens to facilitate circulation of heat exchange fluid through the balloon 22.

The catheter 10 includes an infusion source 27 in communication with the catheter body 14 for infusing fluids such as medicine via the catheter 10 and into the patient.

Figure 2:
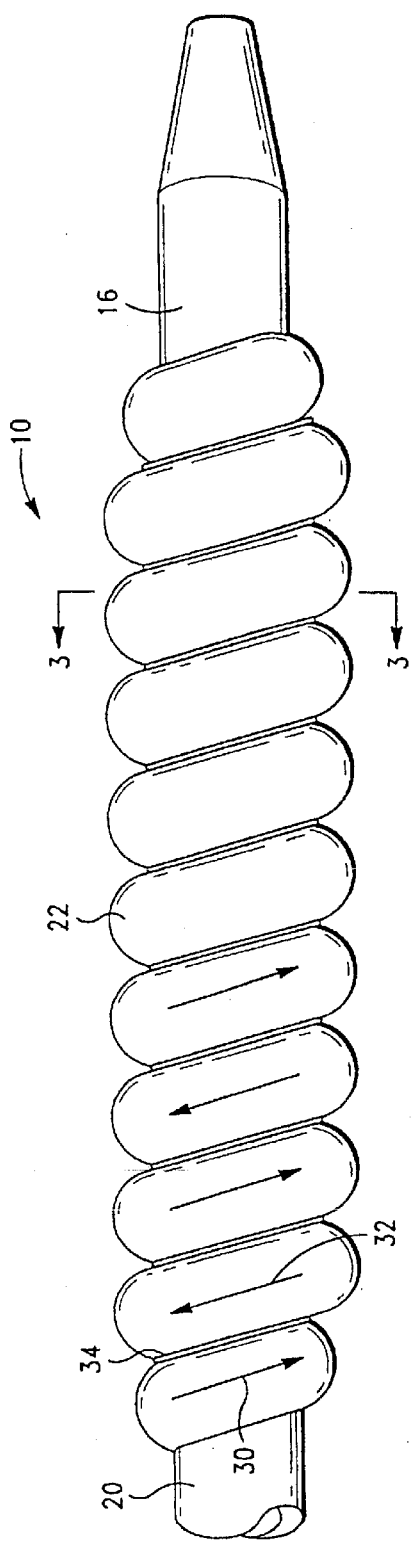
FIG. 2 shows the distal end of a catheter.

FIG. 2 shows the distal end 16 of the catheter 10. The balloon 22 defines a double helix that wraps tightly on the core 20. The double helix configuration enables the direction of inflow of heat exchange fluid as shown by the arrow 30 to oppose the direction outflow of heat exchange fluid as shown by the arrow 32. The opposing flow directions enable a more uniform heat transfer temperature range between the balloon 22 and flowing blood.

The catheter 10 includes a wire 34 wrapped around the balloon 22 to seal the balloon 22 against the core 20 along a helical path. The wire 34 isolates the portions of the balloon having inflow of heat exchange fluid from the portions of the balloon having outflow of heat exchange fluid. The wire 34 maintains the balloon in the double helix configuration. Wrapping the wire 34 around the balloon 22 to tightly seal the balloon 22 against the core 20 along a helical path favorably effects the bending characteristics of the distal end 16, making the end 16 more flexible.

Figure 3B:
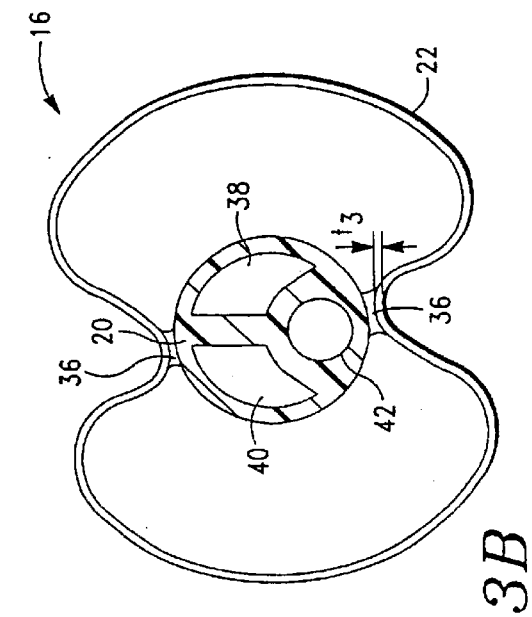
FIG. 3B shows an embodiment of the cross-section of the distal end as seen along the line 3—3 of FIG. 2.
Figure 3A:
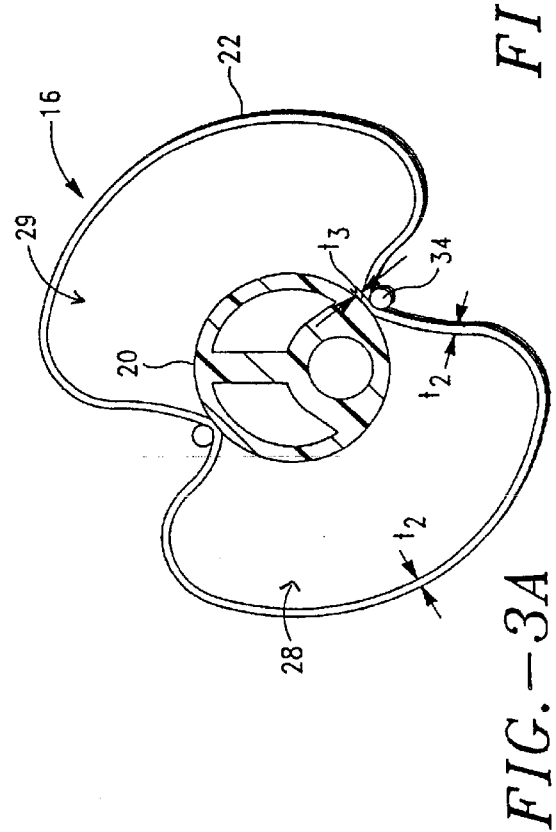
FIG. 3A shows an embodiment of the cross-section of the distal end as seen along the line 3—3 of FIG. 2.

FIG. 3A shows one embodiment of a cross-section of the distal end 16 as seen along the line 3—3 of FIG. 2. The balloon 22 has nominal wall thickness $t_1$. The wall thickness $t_1$ thickens as the balloon 22 nears the core 20 and the region where the balloon 22 thickens is designated by the symbol $t_2$. The balloon 22 contacts the core 20 on opposing sides of the core and where the balloon 22 contacts the core 20, the thickness of the balloon 22 is at a maximum thickness as designated with the symbol $t_3$. The wire 34 wraps the balloon 22 to the core 20 at the thickest portion of the balloon 22, i.e. where the balloon 22 achieves the highest degree of structural integrity. The wire 22 seals against the balloon 22 to cause the balloon 22 to form two discrete lumens 28 and 29.

Situating the thickest part of the balloon 22, having a thickness $t_3$, close to the core 20 minimizes any stiffening influence that the thickest part of the balloon has on the proximal end 16. Thinning the balloon 22 away from the core minimizes stiffening influence that of the balloon 22 has on the proximal end 16.

FIG. 3B shows another embodiment of a cross-section of the distal end 16 as seen along the line 3—3 of FIG. 2. Adhesive 36 joins the thickest part of the balloon 22, having a thickness $t_3$, with opposing sides of the core 20. Adhesively joining the balloon 22 to the core at the thickest part of the balloon 22 assures structural integrity of the balloon 22 at the core 20. It can be appreciated that adhesive 36 can be used in conjunction with the wire 34 to join the balloon 22 with the core 20.

The core 20 defines a heat exchange fluid inlet lumen 38, a heat exchange fluid outlet lumen 40 that function to achieve the heat exchange fluid flow as denoted by the arrows 30 and 32 of FIG. 2.

The core 20 includes a guidewire lumen 42 connectable with an infusion source 27 (FIG. 1) for delivering medicine to the vasculature 12 of the patient via the guidewire lumen 42.

FIGS. 4A–4C show pre-assembly components of one embodiment of the catheter 10. FIG. 4A particularly shows a portion of the balloon 22 having a pre-formed nominal surface contour. The nominal surface contour resembles a double helix to enable a wire to readily and securely mate with the balloon 22.

The balloon 22 has a hollow interior nominally forming a single lumen. It can be appreciated, however, that according to another aspect of the invention, the balloon 22 can also have a nominal shape resembling a cylinder. The double helix shape is preferred, however, to achieve desired balloon 22 thickness when the balloon 22 mounts on the a core.

FIG. 4B shows a portion of the core 20. The core 20 includes an outlet port 44 that communicates with the inlet lumen 38 for delivering heat exchange fluid out of the core 20 and into a lumen of a heat exchange balloon. The core 20 includes an inlet port 46 for receiving heat exchange fluid from a lumen of a heat exchange balloon. The core 20 includes an outlet port 40 in communication with the inlet port 46 to enable the inlet port 46 to pass heat exchange fluid via the core 20 out to a lumen of a heat exchange balloon. The core 20 includes an inlet port 50 in communication with the outlet lumen 40 for returning heat exchange fluid to a heat exchange fluid source.

FIG. 4C shows the wire 34 having a generally helical shape. According to one aspect of the invention, the wire 34 is elastic to stretch and hold the balloon 22 on the core 20 (FIG. 2). The wire 34 has two ends 52 and 54 that attach to the core 20 when the wire 34 wraps around the core 20.

Assembling the Catheter

A method of assembling a heat exchange catheter includes providing a catheter body having a proximal end and surrounding a portion of the proximal end with a balloon having a hollow interior.

Next, the method includes wrapping a wire wrapping around the balloon to seal the balloon against the core, thus defining at least two lumens between the balloon and the core. In this way, the core and the balloon cooperate to define at least two lumens for circulating heat exchange fluid.

According to one aspect of the invention, the balloon has a nominal shape resembling a double helix so that the wire more easily seals the balloon to the core. The double helix resembling nominal shape enables the balloon to have a variable thickness where the thickest part of the balloon is near the core and the thinnest part is radially distant from the core.

Adhesive bonds a portion of the balloon to the core according to one aspect of the invention to further thicken the thickest part of the balloon, near the core and being surrounded by the wire. The adhesive cooperates with the thickest part of the core to improve the structural integrity of the balloon.

When the wire wraps around the balloon in a helical path and maintains the balloon in a helical shape. Accordingly, the balloon may have an alternate nominal configuration where the balloon has a generally cylindrical shape and relies solely on the wire to seal the balloon against the core.

It is preferred, however, that the balloon be pre-formed, having a nominal surface contour resembling a helix to enable the wire to securely mate with the balloon. This nominal surface contour is shown in FIG. 4A and can be achieved by heat treating the balloon during fabrication.

There are many alternatives to the wire and adhesive used to seal the balloon to the core. For example, the wire can be shaped in a non-uniform helical pattern, or assume a flattened or otherwise configured cross-section. The balloon thickness can vary. Further, the core may be constructed having more, or less lumens to accommodate any of a number of uses for the catheter. For example, the core lumens may be configured for guiding diagnostic, or operative tools, into the vasculature of a patient. Accordingly, the present invention is to be limited only by the appended claims.

We claim:

1. An intravascular heat exchange catheter comprising:
   a catheter body having a proximal end connectable with a heat exchange fluid source and a distal end insertable into the vasculature of a patient to facilitate heat transfer with flowing blood;
   a core defining at least one heat exchange fluid lumen for circulating heat exchange fluid within the catheter body;
   a balloon surrounding a portion of the proximal end and being in fluid communication with the heat exchange fluid lumen for enabling heat exchange fluid from the heat exchange fluid source to circulate through the core and the balloon; and
   a wire wrapping around the balloon to seal the balloon against the core.

2. A catheter as set forth in claim 1, wherein the wire has a helical configuration to seal the balloon against the core along a helical path.

3. A catheter as set forth in claim 2, further comprising adhesive to bond the helical path of the balloon to the core so that the wire and the adhesive cooperate to maintain the balloon in a helical shape.

4. A catheter as set forth in claim 3, wherein the balloon is tubular in shape, having a nominal surface contour, the surface contour resembling a helix to enable the wire to securely mate with the balloon.

5. A catheter as set forth in claim 1, further comprising a guidewire lumen.

6. A catheter as set forth in claim 1, further comprising a guidewire lumen connectable with an infusion source for delivering medicine to the vasculature of the patient via the guidewire lumen.

7. A intravascular heat exchange catheter comprising:
   a catheter body having a proximal end connectable with a heat exchange fluid source and a distal end insertable into the vasculature of a patient to facilitate heat transfer with flowing blood;
   a core defining heat exchange fluid inlet lumen and a heat exchange fluid outlet lumen for circulating heat exchange fluid within the catheter body;
   a balloon having a non-uniform wall thickness surrounding a portion of the proximal end and being in fluid communication with the core for enabling heat exchange fluid from the heat exchange fluid source to circulate heat exchange fluid through the core and the balloon; and
   a wire wrapping around the balloon to seal the balloon against the core and to cause the balloon to define at least two lumens.

8. A catheter as set forth in claim 7, wherein the wire has a helical configuration to seal the balloon against the core along a helical path.

9. A catheter as set forth in claim 8, further comprising adhesive to bond the helical path of the balloon to the core so that the wire and the adhesive cooperate to maintain the balloon in a helical shape.

10. A catheter as set forth in claim 9, wherein the balloon is tubular in shape, having a nominal surface contour, the surface contour resembling a helix to enable the wire to securely mate with the balloon.

11. A catheter as set forth in claim 7, further comprising a guidewire lumen.

12. A catheter as set forth in claim 11, wherein the guidewire lumen is connected with an infusion source for delivering medicine to the vasculature of the patient via the guidewire lumen.

13. A method of assembling an intravascular heat exchange catheter comprising:
   providing a catheter body having a proximal end, a core defining at least one heat exchange fluid lumen, and a distal end;
   surrounding a portion of the proximal end with a balloon; and
   wrapping a wire wrapping around the balloon to seal the balloon against the core.

14. The method as set forth in claim 13, further comprising bonding a portion of the balloon to the core.

15. The method as set forth in claim 13, wherein the wire wraps around the balloon in a helical path.

16. The method as set forth in claim 15, further comprising bonding the balloon to the core along the helical path.

17. The method as set forth in claim 12, further comprising pre-forming the balloon to have a nominal surface contour, the surface contour resembling a helix to enable the wire to securely mate with the balloon.

18. The method as set forth in claim 12, further comprising pre-forming the balloon to have a nominal surface contour, the surface contour resembling a helix to enable the wire to securely mate with the balloon, wherein the step of pre-forming includes heating the balloon.

19. The method as set forth in claim 17, wherein the step of pre-forming the balloon includes pre-forming the balloon with a non-uniform wall thickness.

20. The method as set forth in claim 19, wherein the wall thickness is thickest near the core and thinnest radially away from the core.

* * * * *